United States Patent [19]

Masuko et al.

[11] 4,144,264

[45] Mar. 13, 1979

[54] PROCESS FOR PRODUCING A 3-METHYL-2-(4-HALOPHENYL)BUTYRONITRILE

[75] Inventors: Fujio Masuko, Ibaraki; Kazuhiko Fujiyoshi, Toyonaka; Yoshitaka Ume, Toyonaka; Shinji Nakai, Minoo; Shigeyoshi Kitamura, Toyonaka; Takeaki Umemura, Takarazuka, all of Japan

[73] Assignee: Sumitomo Chemical Company, Limited, Osaka, Japan

[21] Appl. No.: 826,088

[22] Filed: Aug. 19, 1977

[30] Foreign Application Priority Data

Aug. 23, 1976 [JP] Japan ................................ 51-100916

[51] Int. Cl.$^2$ ............................................. C07C 121/66
[52] U.S. Cl. ................................................. 260/465 G

[58] Field of Search ........................ 260/465 G, 465 R

[56] References Cited

U.S. PATENT DOCUMENTS 4,012,428   3/1977   Ohno et al. ...................... 260/465 G Primary Examiner—Dolph H. Torrence
Attorney, Agent, or Firm—Sughrue, Rothwell, Mion, Zinn and Macpeak

[57] ABSTRACT

A process for producing 3-methyl-2-(4-halophenyl)-butyronitrile, which is an important intermediate for the production of insecticides, in a high yield and a high purity even on a commercial scale comprising reacting a p-halophenylacetonitrile having a p-halobenzyl alcohol content of not more than 1.0 % by weight, with an isopropyl halide having an isopropyl alcohol content of not more than 1.0 % by weight.

8 Claims, 2 Drawing Figures

PROCESS FOR PRODUCING A 3-METHYL-2-(4-HALOPHENYL)BUTYRONITRILE

BACKGROUND OF THE INVENTION

1. Field of the Invention

The present invention relates to an improvement in a process for the production of a 3-methyl-2-(4-halophenyl)butyronitrile.

2. Description of the Prior Art

3-Methyl-2-(4-halophenyl)butyronitrile is an important intermediate useful in the production of an insecticide developed recently, e.g., as disclosed in U.S. Pat. No. 3,996,244.

U.S. Pat. No. 4,012,428 summarizes in detail fairly recent prior art approaches toward the alkylation of phenylacetonitrile (e.g., as disclosed in *Organic Reactions*, 9, 297 (1957), *J. Org. Chem.*, 37, 526 (1972), *Tetrahedron Letters*, 473 (1972), *Roczniki Chem.*, 39, 1223 (1965) [*Chemical Abstracts*, 64, 12595 (1965)] and *Roczniki Chem.*, 42, 1619 (1968) [*Chemical Abstracts*, 70, 37413 (1969)] and U.S. Pat. No. 3,996,244) and discloses an improved process for the production of a 3-methyl-2-(4-halophenyl)butyronitrile comprising reacting a p-halophenylacetonitrile with an isopropyl halide in an aqueous solution of an alkali metal hydroxide using, as a specific catalyst, a quaternary organoammonium salt. Even this process disclosed in U.S. Pat. No. 4,012,428 is, however, not always satisfactory industrially particularly from the standpoint of reproducibility.

Intensive investigations have now been made to discover a process for producing 3-methyl-2-(4-halophenyl)butyronitrile in a high yield and a high purity even on a commercial scale. Surprisingly it has been found that the reaction between the p-halophenylacetonitrile and the isopropyl halide to produce 3-methyl-2-(4-halophenyl)butyronitrile is adversely affected by p-halobenzyl alcohol and isopropyl alcohol which are inevitably present as by-products in the production of the p-halophenylacetonitrile and isopropyl halide, respectively. More specifically, p-halophenylacetonitrile is produced industrially by the reaction between the corresponding p-halobenzyl halide and sodium cyanide under alkaline conditions, which is accompanied by the by-production of p-halobenzyl alcohol due to the hydrolysis of the halogen attached to the benzyl moiety, and isopropyl halide is produced industrially by a halogenation of isopropyl alcohol or a hydrogen halide-addition to propylene, which is accompanied by unreacted isopropyl alcohol remaining or the production of isopropyl alcohol as a by-product, respectively.

No prior art is known including U.S. Pat. No. 4,012,428 which discloses that the alcohols inevitable present in the starting materials, p-halophenylacetonitrile and isopropyl halide, have an inhibitory effect on the reaction to produce 3-methyl-2-(4-halophenyl)-butyronitrile therefrom. Accordingly, the production of the desired 3-methyl-2-(4-halophenyl)butyronitrile has been carried out using p-halophenylacetonitrile and isopropyl halide, both of which contain several % by weight of the corresponding alcohols, and, as a result, the desired product cannot be produced with good reproducibility. Large amounts of unreacted feed materials, by-products and decomposition products resulting from the low reactivity due to the inhibitory action of these alcohols complicate the subsequent purification process, and moreover, adversely influence the quality of the final insecticide produced therefrom as well as the insecticidal effect thereof.

SUMMARY OF THE INVENTION

Accordingly, an object of the present invention is to provide a process for the production of the desired 3-methyl-2-(4-halophenyl)butyronitrile in a high yield and a high purity with a good reproducibility.

The above described and other objects are achieved by the present invention which provides a process for producing a 3-methyl-2-(4-halophenyl)butyronitrile comprising reacting a p-halophenylacetonitrile with a p-halobenzyl alcohol content of not more than 1% by weight with an isopropyl halide with an isopropyl alcohol content of not more than 1% by weight in the presence of a quaternary organoammonium salt as a catalyst and a base.

BRIEF DESCRIPTION OF THE ACCOMPANYING DRAWINGS

DETAILED DESCRIPTION OF THE INVENTION

The starting materials, the p-halophenylacetonitrile and the isopropyl halide, which have been produced on a commercial scale, inevitably are contaminated with several % by weight or more of the corresponding alcohols. Accordingly, in the present invention, prior to the reaction the starting materials are pre-treated to reduce the content of the inhibitory alcohol materials, the p-halobenzyl alcohol and the isopropyl alcohol, to 1% by weight or less based on the weight of the starting materials, respectively. In other words, the inhibitory alcohol materials must be removed from the starting materials in a suitable manner.

The alcohols can be removed from the starting materials using various known methods. Isopropyl alcohol can be removed from the isopropyl halide, for example, by washing the starting isopropyl halide with water or mineral acids such as hydrochloric acid and sulfuric acid or by using a rectification. The p-halobenzyl alcohol can be removed from the p-halophenylacetonitrile, for example, by using a crystallization or a rectification.

Figure 1:
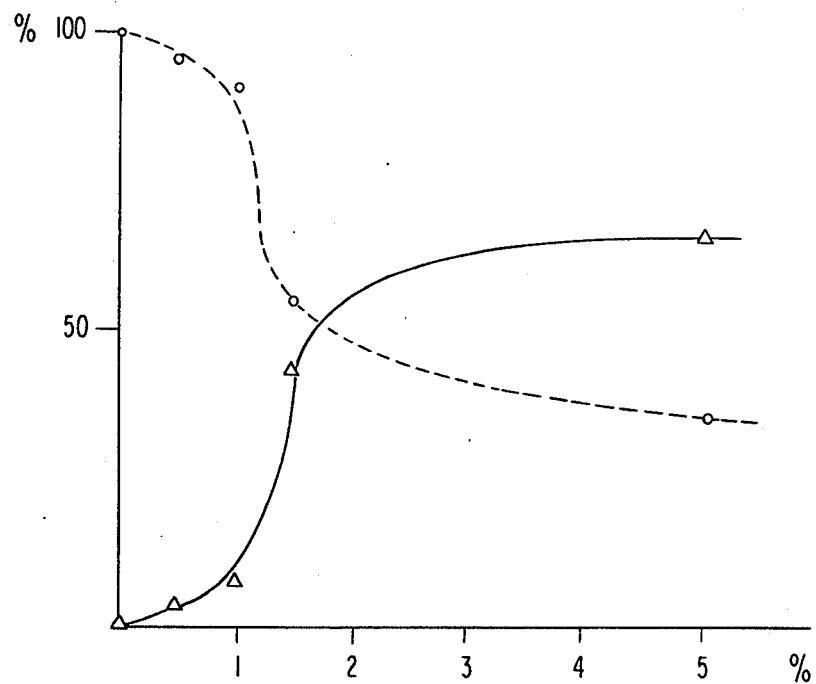
FIG. 1 shows the influence of isopropyl alcohol content on the reaction between p-chlorophenylacetonitrile and isopropyl chloride.

Turning now to FIG. 1 the area percentage determined by gas chromatography is shown as the ordinate, and the isopropyl alcohol content in the isopropyl chloride feed is shown as the abscissa in terms of % by weight. The solid line and the dotted line represent the amounts of p-chlorophenylacetonitrile and 3-methyl-2-(4-chlorophenyl)butyronitrile, respectively. The reaction conditions are the same as in Example 1, except that the reaction time and temperature were 6 hours and 35° C., respectively.

As is evident from FIG. 1, when the isopropyl alcohol content in the isopropyl chloride feed exceeds 1% by weight, the conversion of p-chlorophenylacetonitrile decreases drastically, with an accompanying decrease in the yield of 3-methyl-2-(4-chlorophenyl)-butyronitrile.

It is apparent that the acceptable content of isopropyl alcohol is up to 1% by weight, preferably up to 0.5% by weight, based on the weight of the isopropyl chloride feed. If a large amount of unreacted p-chlorophenylacetonitrile remains due to the inhibitory action of isopropyl alcohol, it is difficult to carry out a rectification on a commercial scale, because of the small difference between the boiling points of these two compounds.

Figure 2:
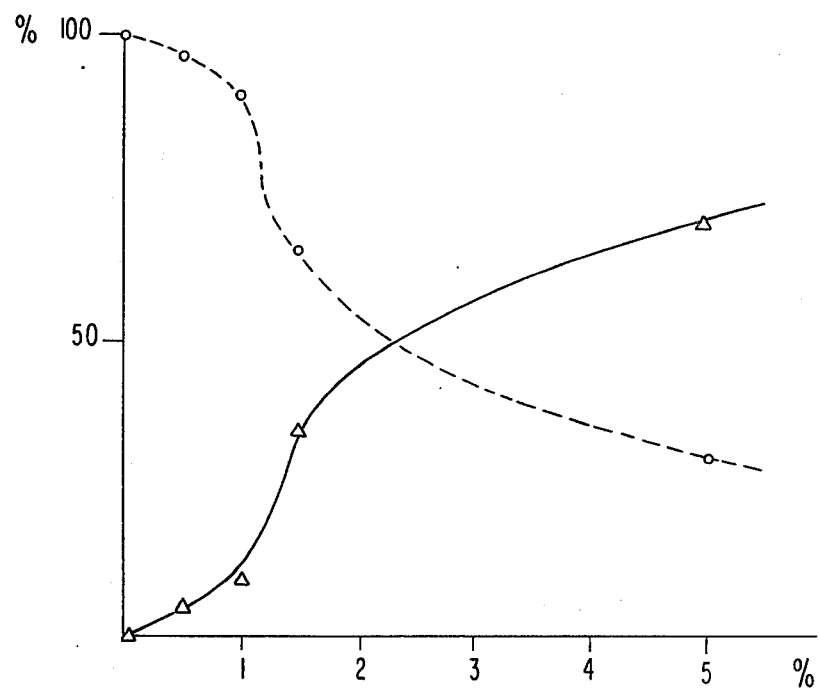
FIG. 2 shows the influence of the p-chlorobenzyl alcohol content on this reaction.

In FIG. 2, the area percentage determined by gas chromatography is shown as the ordinate, and the p-chlorobenzyl alcohol content in the p-chlorophenylacetonitrile feed is shown as the abscissa in terms of % by weight. The solid line and dotted line represent the amounts of p-chlorophenylacetonitrile and 3-methyl-2-(4-chlorophenyl)butyronitrile, respectively. The reaction conditions were the same as in Example 1, except that the reaction time and temperature were 6 hours and 40° to 42° C., respectively.

As is evident from FIG. 2, when the p-chlorobenzyl alcohol content in the p-chlorophenylacetonitrile feed exceeds 1% by weight, the conversion of p-chlorophenylacetonitrile decreases drastically, naturally with an accompanying decrease in the yield of 3-methyl-2-(4-chlorophenyl)butyronitrile. There are serious problems due to unreacted p-chlorophenylacetonitrile remaining as in the case of isopropyl alcohol described above.

Alcohols other than those described above, which have a tendency to also be present in the feed materials and be present during the operations, have an inhibitory action in the reaction, and, therefore, attention should be paid to avoid this type of contamination as well.

As described above, the process of this invention provides a marked improvement in the yields and purity obtained and reproducibility achieved in the process for producing 3-methyl-2-(4-halophenyl)butyronitrile as described in U.S. Pat. No. 4,012,428, the disclosure relative to which process is incorporated herein by reference.

More specifically, in carrying out the process of the present invention, suitable starting materials which can be employed are, i.e., p-halophenylacetonitriles including p-chlorophenylacetonitrile and p-bromophenylacetonitrile, and isopropyl halides including isopropyl chloride and isopropyl bromide.

The process of the present invention is carried out in the presence of a quaternary organoammonium salt as a catalyst and a base. Examples of suitable quaternary organoammonium salts which can be employed as the catalyst include tetra-n-butylammonium chloride, tetra-n-butylammonium bromide, tetraethylammonium chloride, tetraethylammonium bromide, triethylbenzylammonium chloride, triethylbenzylammonium bromide, p-chlorobenzyltriethylammonium chloride and p-chlorobenzyltriethylammonium bromide, which may be used individually or as a combination thereof.

The amount of the catalyst employed is 1/200 mole to 1/5 mole per mole of the p-halophenylacetonitrile.

Suitable bases which can be used include an aqueous solution of alkali metal hydroxides such as sodium hydroxide and potassium hydroxide, alkali metal hydrides such as sodium hydride, and alkali metals such as potassium and sodium. The amount of the base is 1 to 8 moles, preferably 2 to 5 moles, per mole of the p-halophenylacetonitrile. A suitable concentration of the aqueous solution of alkali metal hydroxides ranges from 10% to 70% by weight, preferably from 40% to 60% by weight. Lower concentrations will result in a decrease in the reaction rate.

The reaction temperature ranges from room temperature (about 20° C.) to about 120° C., favorably about 30° to about 60° C.

The isopropyl halide is used in an amount of at least one mole, preferably 1.0 to 10 moles, per mole of the p-halophenylacetonitrile. An excess of the isopropyl halide can be used as a solvent.

The reaction between the p-halophenylacetonitrile and the isopropyl halide can be carried out in the presence or absence of a solvent. Suitable solvents which can be used, preferably are inert solvents such as benzene and toluene.

The present invention is explained in more detail by reference to the following Reference Examples and Examples, which are only illustrative and are not to be construed as limiting the scope of the present invention.

Unless otherwise indicated, all parts, percents, ratios and the like are by weight.

EXAMPLE 1

In a reaction vessel were placed 120.5 g of a 53% aqueous sodium hydroxide solution (1.65 moles) and 3.89 g (0.01207 mole) of tetra-n-butylammonium bromide, and then the temperature was maintained at 40° to 42° C. 60.6 grams (0.40 mole) of p-chlorophenylacetonitrile having a p-chlorobenzyl alcohol content of 0.1% by weight, and 125.6 g (1.60 moles) of isopropyl chloride having an isopropyl alcohol content of 0.1% by weight were added dropwise thereto simultaneously over a period of 3 hours. Thereafter, the reaction temperature was kept at 42° C., and reflux was continued for 3 hours.

The reaction mixture was cooled to below 30° C. and poured into 100 g of water. The organic layer, which separated from the aqueous layer, was mixed with 100 g of water. The organic layer again separated was concentrated under atmospheric pressure to recover 86.7 g of isopropyl chloride. The recovery was 92%.

The amount of the resulting concentrate obtained was 75.1 g and the resulting concentrate was gas-chromatographically found to be a mixture of 71.1 g of the desired 3-methyl-2-(4-chlorophenyl)butyronitrile, 0.38 g of unreacted p-chlorophenylacetonitrile, 0.90 g of 3-methyl-2-isopropyl-2-(4-chlorophenyl)butyronitrile and 2.7 g of other materials.

The yield of 3-methyl-2-(4-chlorophenyl)acetonitrile calculated on the basis of p-chlorophenylacetonitrile was 93%.

EXAMPLE 2

The procedures of Example 1 were repeated, except that the reaction was carried out at 35° C. using p-chlorophenylacetonitrile having a p-chlorobenzyl alcohol content of 0.3% by weight, and isopropyl chloride having an isopropyl alcohol content of 0.3% by weight. The time required for completion of the reaction was 7 hours.

The amount of resulting product obtained was 75.9 g and the resulting product contained 72.1 g (yield 94%) of the desired 3-methyl-2-(4-chlorophenyl)butyronitrile.

REFERENCE EXAMPLE 1

The procedures of Example 1 were repeated, except that the reaction was carried out using p-chlorophenylacetonitrile having a p-chlorobenzyl alcohol content of 0.1% by weight, and isopropyl chloride having an isopropyl alcohol content of 1.5% by weight.

The reaction was carried out for a prolonged period of 12 hours, but the yield of 3-methyl-2-(4-chlorophenyl)butyronitrile reached only 50%, leaving 50% unreacted p-chlorophenylacetonitrile.

REFERENCE EXAMPLE 2

The procedures of Example 1 were repeated, except that the reaction was carried out using p-chlorophenylacetonitrile having a p-chlorobenzyl alcohol content of 1.5% by weight, and isopropyl alcohol having an isopropyl alcohol content of 0.1% by weight.

The reaction was carried out for a prolonged period of 12 hours, but the yield of 3-methyl-2-(4-chlorophenyl)butyronitrile reached only 60%. The remainder was found to be unreacted starting materials.

While the invention has been described in detail and with reference to specific embodiments thereof, it will be apparent to one skilled in the art that various changes and modifications can be made therein without departing from the spirit and scope thereof.

What is claimed is:

1. In a process for producing 3-methyl-2-(4-halophenyl)butyronitrile on a large scale utilizing as starting materials p-halophenylacetonitrile containing a substantial amount of p-halobenzyl alcohol as an impurity therein and an isopropyl halide containing a substantial amount of isopropyl alcohol as an impurity therein, said process comprising reacting said p-halophenylacetonitrile with said isopropyl halide in the presence of a base and a quaternary organoammonium salt as a catalyst, the improvement comprising reducing the p-halobenzyl alcohol content of said p-halophenylacetonitrile to not more than 1% by weight and the isopropyl alcohol content of said isopropyl halide to not more than 1% by weight prior to said reaction.

2. The process according to claim 1, wherein the quaternary organoammonium salt is tetra-n-butylammonium chloride, tetra-n-butylammonium bromide, tetraethylammonium chloride, tetraethylammonium bromide, triethylbenzylammonium chloride, triethylbenzylammonium bromide, p-chlorobenzyltriethylammonium chloride, p-chlorobenzyltriethylammonium bromide, or a mixture thereof.

3. The process according to claim 1, wherein the quaternary organoammonium salt is present in an amount of 1/200 mole to 1/5 mole per mole of the p-halophenylacetonitrile.

4. The process according to claim 1, wherein the isopropyl halide is present in an amount of at least one mole per mole of the p-halophenylacetonitrile.

5. The process according to claim 1, wherein the reaction is conducted at a temperature of from room temperature to about 120° C.

6. The process according to claim 1, wherein the p-halophenylacetonitrile is p-chlorophenylacetonitrile or p-bromophenylacetonitrile.

7. The process according to claim 1, wherein the isopropyl halide is isopropyl chloride or isopropyl bromide.

8. The process according to claim 1, wherein the base is an alkali metal, an alkali metal hydride or an aqueous solution of an alkali metal hydroxide.

* * * * *